US00PP27081P3

(12) United States Plant Patent
Bak et al.

(10) Patent No.: US PP27,081 P3
(45) Date of Patent: Aug. 23, 2016

(54) ***MEDINILLA* HYBRID PLANT NAMED 'ROYAL FLAZH'**

(50) Latin Name: ***Medinilla* hybrid**
Varietal Denomination: ROYAL FLAZH

(71) Applicants: Elly Bak, Assendelft (NL); Nicolaas D. M. Steur, Oude Niedorp (NL)

(72) Inventors: Elly Bak, Assendelft (NL); Nicolaas D. M. Steur, Oude Niedorp (NL)

(73) Assignee: Corn Bak B.V. (NL)

( * ) Notice: Subject to any disclaimer, the term of this patent is extended or adjusted under 35 U.S.C. 154(b) by 141 days.

(21) Appl. No.: 13/999,980

(22) Filed: Apr. 11, 2014

(65) Prior Publication Data

US 2015/0296675 P1 Oct. 15, 2015

(51) Int. Cl.
*A01H 5/02* (2006.01)

(52) U.S. Cl.
USPC ..... Plt./226

(58) Field of Classification Search
USPC ..... Plt./226, 263.1
See application file for complete search history.

*Primary Examiner* — Keith Robinson
(74) *Attorney, Agent, or Firm* — Cassandra Bright

(57) ABSTRACT

A new and distinct *Medinilla* sp. plant named 'ROYAL FLAZH', characterized by a erect to semi-erect plant, measuring about 55-75 cm in total height (when first flowering) and about 75-100 cm in diameter; green colored leaves, measuring about 30-35 cm in length and about 10-15 cm in width; pendulous panicle, measuring about 25-30 cm in length and about 10-15 cm in diameter, with red-purple (RHS 67B) flowers.

2 Drawing Sheets

Latin name of the genus and species: *Medinilla* hybrid.
Variety denomination: 'ROYAL FLAZH'.

BACKGROUND OF THE INVENTION

The present invention relates to a new and distinct hybrid cultivar of *Medinilla* plant, botanically known as *Medinilla* hybrid, hereinafter referred to by the cultivar name 'ROYAL FLAZH'. The genus of *Medinilla* belongs to the Melastomataceae family.

*Medinilla* 'ROYAL FLAZH' is a product of a planned breeding program conducted by the inventors, Elly Bak and Nico D. M. Steur, in Assendelft, the Netherlands. The objective of the breeding program is to develop new *Medinilla* varieties with good growing habits and attractive inflorescence.

The new *Medinilla* 'ROYAL FLAZH' originated from a crossing made in a controlled breeding program by the inventors in 2005 in Assendelft, the Netherlands. The female or seed parent is the *Medinilla* selection designated '82797015' (unpatented), and the male or pollen parent is the *Medinilla* selection designated '82796501' (unpatented). 'ROYAL FLAZH' was discovered and selected by the inventors in 2007, as a single flowering plant within the progeny of the stated cross in a controlled environment in Assendeift, the Netherlands.

Asexual reproduction of the new *Medinilla* hybrid 'ROYAL FLAZH' performed by vegetative means by cuttings was first performed in 2007, in Assendeift, The Netherlands. The first 'ROYAL FLAZH' plants propagated through the use of cuttings flowered in 2008, in Assendeift, The Netherlands, and have demonstrated that the combination of characteristics as herein disclosed for the new cultivar are firmly fixed and retained through successive generations of asexual reproduction. The new cultivar reproduces true-to-type.

BRIEF DESCRIPTION OF THE INVENTION

The following traits have been repeatedly observed and are determined to be 30 unique characteristics of 'ROYAL FLAZH' which in combination distinguish this *Medinilla* hybrid as a new and distinct cultivar:

1. Solid growth habit.
2. Erect to semi-erect plant measuring approximately 55 to 75 cm from the soil line, when flowering first begins.
3. Bright green leaves measuring approximately 30 to 35 cm in length and approximately 15 cm in width.
4. Pendulous panicles with red-purple (RHS 67B) colored flowers.

COMMERCIAL COMPARISON

Of the many commercial cultivars known to the present inventors, the most similar in comparison to the new *Medinilla* 'ROYAL FLAZH' is the *Medinilla* 'BELO', unpatented. Plants of the new *Medinilla* 'ROYAL FLAZH' differ from plants of *Medinilla* 'BELO' primarily in leaf size, and inflorescence length. Plants of 'ROYAL FLAZH' have smaller leaves than plants of 'BELO'. Additionally, inflorescences of 'ROYAL FLAZH' are longer and more open.

COMPARISON WITH THE PARENT VARIETIES

Plants of the new *Medinilla* 'ROYAL FLAZH' are similar to the seed parent in most horticultural characteristics. The new variety 'ROYAL FLAZH' however, differs from plants of the seed parent in the following:

1. Inflorescence color of the seed parent variety is significantly lighter red-purple than that of the new variety.

Plants of the new *Medinilla* 'ROYAL FLAZH' are similar to plants of the pollen parent in most horticultural characteristics. The new variety 'ROYAL FLAZH' however, differs from plants of the pollen parent in the following:

1. Inflorescence of the pollen parent variety is smaller than that of the new variety.

BRIEF DESCRIPTION OF THE PHOTOGRAPHS

The accompanying photographs illustrate the overall appearance of the new *Medinilla* 'ROYAL FLAZH' showing the colors as true as is reasonably possible with colored reproductions of this type. Colors in the photograph may differ slightly from the color values cited in the detailed botanical description which accurately describes the color of 'ROYAL FLAZH'.

DETAILED BOTANICAL DESCRIPTION

Figure 1:
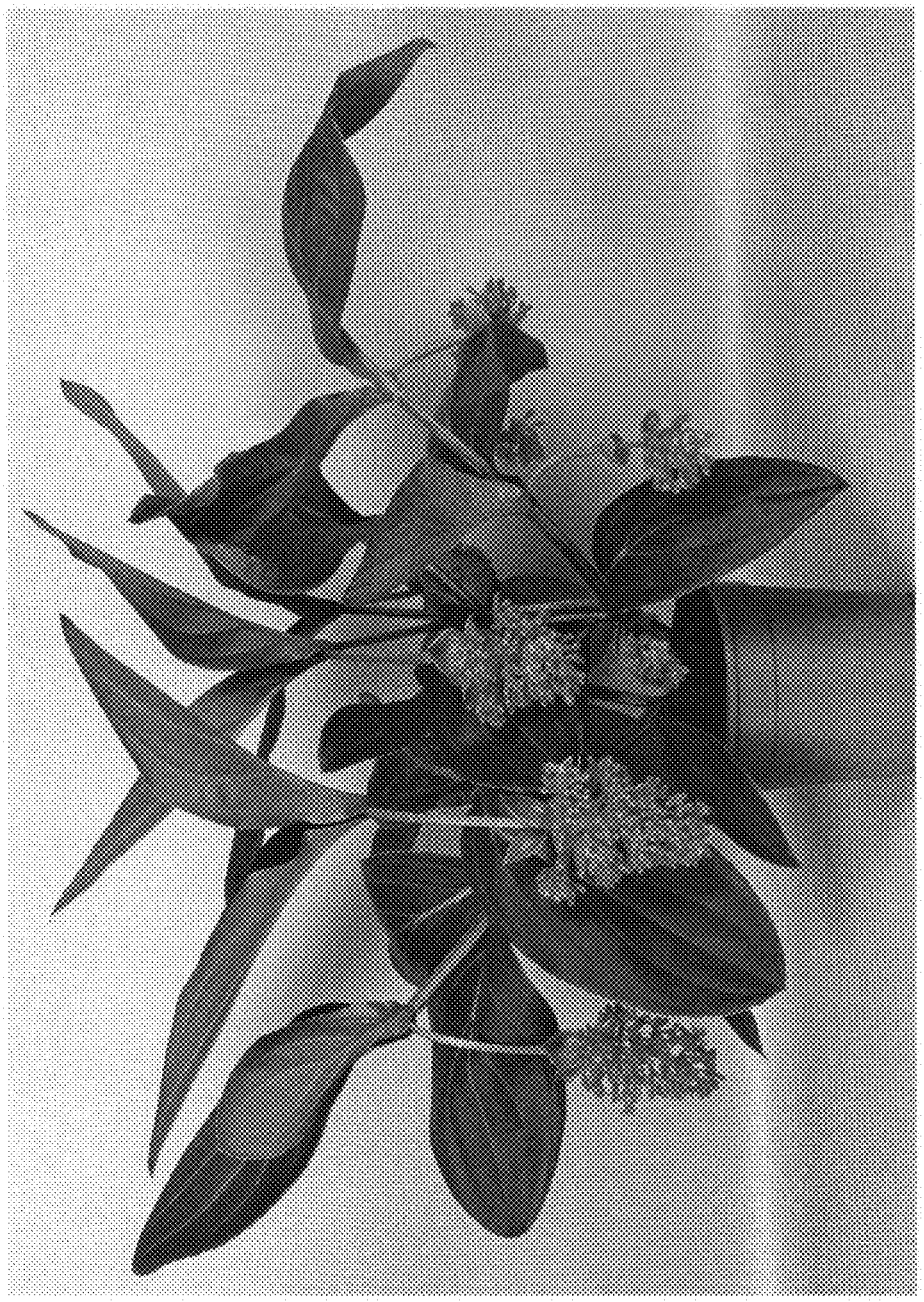
FIG. 1 shows a side view perspective of a typical potted flowering plant of 'ROYAL FLAZH' at about 50 weeks from potting.
Figure 2:
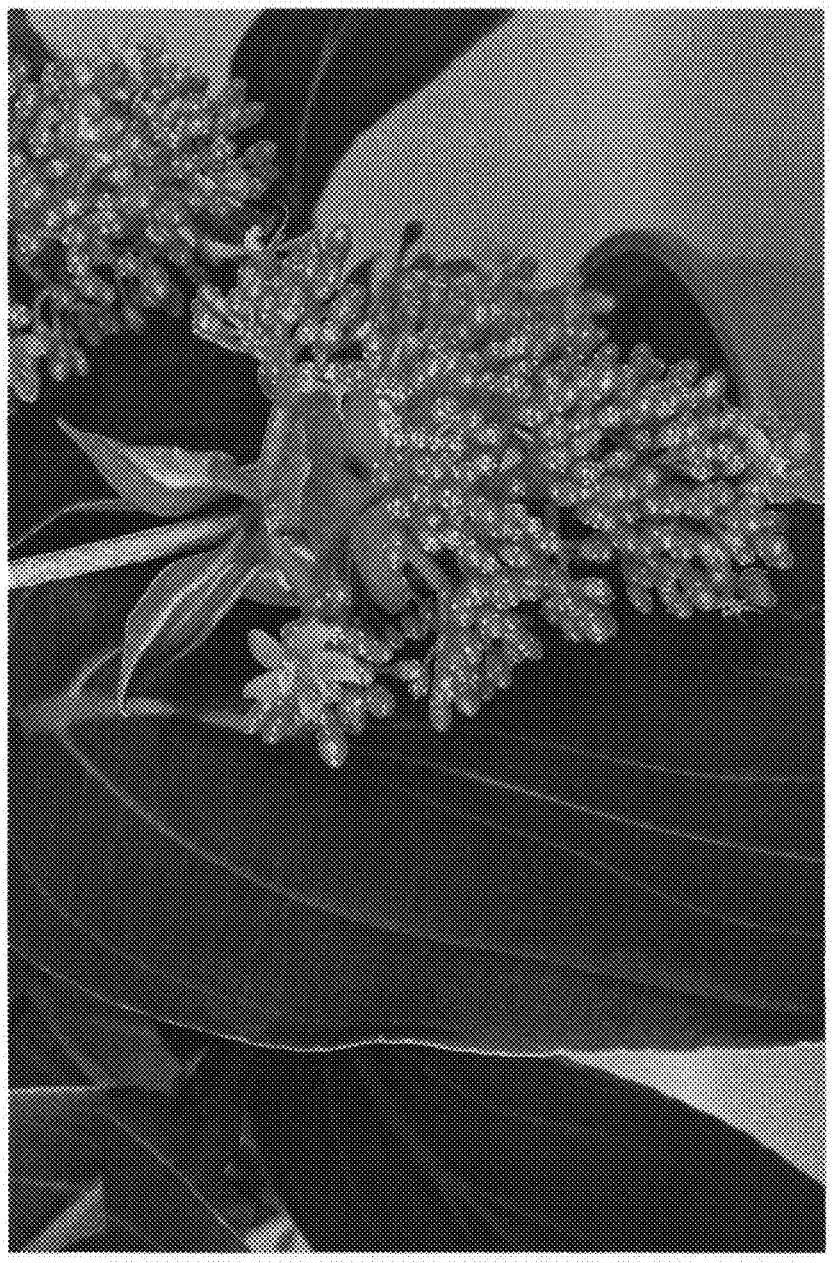
FIG. 2 shows a side view of the inflorescence.

'ROYAL FLAZH' has not been observed under all possible environmental conditions. The phenotype of the new cultivar may vary with variations in environment such as temperature, light intensity, day length, fertilizers and humidity without any change in the genotype of the plant.

The aforementioned photographs, together with the following observations, measurements and values describe the new *Medinilla* 'ROYAL FLAZH' as grown in a greenhouse in Assendelft, The Netherlands, under conditions which closely approximate those generally used in commercial practice.

Color references are made to The Royal Horticultural Society Colour Chart (R.H.S.), 2001 Edition, except where general colors of ordinary significance are used. Color values were taken under daylight conditions in a greenhouse in Assendelft, The Netherlands. The age of the plants of 'ROYAL FLAZH' described is about 50 weeks from potting.

Classification:

*Botanical.*—*Medinilla* hybrid.

Parentage:

*Female parent.*—*Medinilla* selection designated '82797015' (unpatented).

*Male parent.*—*Medinilla* selection designated '82796501' (unpatented).

Propagation: Cuttings.

Plant:

*General appearance and form.*—Inverted "V" shape, with upright and semi-upright straight stems. Height: About 55-75 cm. Diameter: About 75-100 cm.

*Plant vigor.*—Good vigor for plant category.

*Flowering season.*—From April until October.

*Cold tolerance.*—Frost tender, temperatures below 5° C. may damage plants.

*Stem.*—Length: Average range 15 to 25 cm. Diameter: Approximately 0.8 to 1.2 cm. Color: Near RHS Green 143C, flushed near Red 53D.

*Fragrance.*—None.

Foliage:

*Arrangement.*—Opposite.

*Attachment.*—Sessile.

*Quantity.*—About 40.

*Size.*—Length: About 30-35 cm. Width: About 10-15 cm.

*Overall shape.*—Elliptical. Apex Shape: cuspidate. Base Shape: acute. Margin: slightly undulate.

*Texture.*—Smooth, all surfaces.

*Color.*—Leaf color can vary somewhat depending on growing conditions. Upper Surface: Glossy green, closest to RHS 139A. Lower Surface: Green, closest to RHS 143A.

*Venation.*—Pinnate, sunken below surface of leaf.

Inflorescence:

*Shape.*—Pendulous panicles.

*Amount.*—About 6-10 (depending on the size of the plant).

*Size.*—Length: About 25-30 cm. Width: About 10-15 cm.

*Color.*—Red-purple, closest to RHS 67B.

*Corolla.*—Number: about 125-200 per panicle.

*Flower bud.*—Length: About 1.0 cm. Diameter: About 6 mm. Color: Near RHS Red 54A.

*Petals.*—Number: 5 per flower. Length: 10 mm. Width: 8 mm. Overall Shape: obovate, asymmetrical. Apex Shape: obtuse. Color: Upper surface: red-purple, closest to RHS 67B. Lower surface: red-purple, closest to RHS 67B.

*Sepals.*—Fused, enclosing the ovary. Color: red-purple, closest to RHS 63B.

*Bracts.*—Quantity: 2 per crown. Arrangement: verticilliate. Size: Length: about 0.5-2.5 mm. Width: less than 1.5 mm. Overall shape: ovate. Color: Near RHS Red 54A.

*Peduncle.*—Length: Average: 15 cm. Diameter: Average range 0.5 to 1.5 cm. Strength: Strong. Texture: Glabrous. Color: Near RHS Red-Purple N57B.

*Pedicels.*—Length: Average: 1.8 cm. Diameter: Average: 0.2 cm. Strength: Moderately strong. Texture: Glabrous. Color: Near RHS Red-Purple N57B.

Reproductive organs:

*Androecium.*—Stamen: Number: 10 per flower. Length: 7 mm. Diameter: 1 mm. Color: light yellow, with a white base (too small to qualify RHS value). Anther: Length: 8 mm. Color: violet, closest to RHS 83B, with a yellow base (too small to qualify RHS value). Pollen: not visible. Gynoecium: Pistil: Number: 1 per flower. Length: 17 mm.

*Stigma.*—Width: <1 mm. Color: white, too small to qualify RHS value. Style: Length: 17 mm. Color: red-purple, closest to RHS 67B. Ovary Shape: round. Position: inferior. Length: 4 mm. Diameter: 4 mm. Color: white, closest to RHS 155C.

Seeds: No seeds produced.

Fruit: No fruit produced.

Disease/pest resistance: No observations made to date.

Disease/pest susceptibility: No observations made to date.

What is claimed is:

1. A new and distinct *Medinilla* plant named 'ROYAL FLAZH', as illustrated and described herein.

* * * * *